US009274072B2

(12) United States Patent
Veirman et al.

(10) Patent No.: US 9,274,072 B2
(45) Date of Patent: Mar. 1, 2016

(54) METHOD FOR DETERMINING INTERSTITIAL OXYGEN CONCENTRATION

(75) Inventors: Jordi Veirman, Annecy le Vieux (FR); Sebastien Dubois, Scionzier (FR); Nicolas Enjalbert, Burlats (FR)

(73) Assignee: COMMISSARIAT À L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 326 days.

(21) Appl. No.: 14/111,974

(22) PCT Filed: Apr. 13, 2012

(86) PCT No.: PCT/FR2012/000144
§ 371 (c)(1),
(2), (4) Date: Oct. 15, 2013

(87) PCT Pub. No.: WO2012/140340
PCT Pub. Date: Oct. 18, 2012

(65) Prior Publication Data
US 2014/0033797 A1 Feb. 6, 2014

(30) Foreign Application Priority Data
Apr. 15, 2011 (FR) ...................... 11 01190

(51) Int. Cl.
*G01N 27/04* (2006.01)
*H01L 21/66* (2006.01)
(Continued)

(52) U.S. Cl.
CPC ................. *G01N 27/041* (2013.01); *G01J 3/42* (2013.01); *G01N 27/125* (2013.01); *H01L 22/12* (2013.01); *H01L 21/3225* (2013.01)

(58) Field of Classification Search
CPC ..... G01N 27/041; G01N 27/04; G01N 27/14; G01N 27/02; H01L 22/12; H01L 22/14
USPC .................. 73/866; 324/451, 719; 374/45
See application file for complete search history.

(56) References Cited

U.S. PATENT DOCUMENTS 4,344,815 A * 8/1982 Cazarra ................. C30B 29/06
117/14
4,637,123 A   1/1987 Cazcarra et al.
(Continued)

FOREIGN PATENT DOCUMENTS

CN          1595625 A      3/2005
CN        101689504 A      3/2010
(Continued)

OTHER PUBLICATIONS

Simoen et al; "Characterisation of oxygen and oxygen-related defects in highly- and lowly-doped silicon;" Materials Science and Engineering B102; 2003; pp. 207-212.
(Continued)

*Primary Examiner* — Peter Macchiarolo
*Assistant Examiner* — Nathaniel Kolb
(74) *Attorney, Agent, or Firm* — Oliff PLC

(57) ABSTRACT

A method for determining the interstitial oxygen concentration of a sample made from a p-doped semiconductor material includes a step of heat treatment of the sample in order to form thermal donors, determining the duration of the heat treatment required to obtain a compensated semiconductor material, determining the thermal donors concentration in the sample of compensated semiconductor material, from the charge carriers concentration, and determining the oxygen concentration from the thermal donors of and the duration of the heat treatment.

19 Claims, 3 Drawing Sheets

(51) Int. Cl.
*G01J 3/42* (2006.01)
*G01N 27/12* (2006.01)
*H01L 21/322* (2006.01)

(56) References Cited

U.S. PATENT DOCUMENTS

| | | | |
|---|---|---|---|
| 5,287,167 | A | 2/1994 | Shirai et al. |
| 6,206,961 | B1 * | 3/2001 | Takeno ............... H01L 21/3225 117/14 |
| 7,297,601 | B2 | 11/2007 | Chidambarrao et al. |
| 7,345,329 | B2 | 3/2008 | Chidambarrao et al. |
| 7,410,846 | B2 | 8/2008 | Chidambarrao et al. |
| 2005/0054145 | A1 | 3/2005 | Chidambarrao et al. |
| 2005/0145992 | A1 | 7/2005 | Chidambarrao et al. |
| 2006/0073649 | A1 | 4/2006 | Chidambarrao et al. |
| 2011/0177682 | A1 | 7/2011 | Falster et al. |

FOREIGN PATENT DOCUMENTS

| | | |
|---|---|---|
| EP | 0165364 B1 | 12/1985 |
| FR | 2 460 479 | 1/1981 |
| JP | 57-12356 | 2/1982 |
| JP | 2005-223098 A | 8/2005 |
| WO | 2010116293 A1 | 10/2010 |

OTHER PUBLICATIONS

Rava et al; "Thermally Activated Oxygen Donors In Si;" 1046 Journal of the Electrochemical Society; Dec. 1982; vol. 129; No. 12; pp. 2844-2849.

Ulyashin et al; "Characterization of the oxygen distribution in Czochralski silicon using hydrogen-enhanced thermal donor formation;" Materials Science and Engineering B73; 2000; pp. 124-129.

Londos et al; "Effect of oxygen concentration on the kinetics of thermal donor formation in silicon at temperatures between 350 and 500 °C;" Appl. Phys Lett; Mar. 29, 1993; vol. 62; No. 13; pp. 1525-1526.

Wijaranakula; "Formation kinetics of oxygen thermal donors in silicon;" Appl. Phys. Lett; Sep. 23, 1991; vol. 59; No. 13; pp. 1608-1610.

Jul. 26, 2012 Search Report issued in International Patent Application No. PCT/FR2012/000144 (with translation).

Jul. 26, 2012 Written Opinion issued in International Patent Application No. PCT/FR2012/000144 (with translation).

* cited by examiner

METHOD FOR DETERMINING INTERSTITIAL OXYGEN CONCENTRATION

BACKGROUND OF THE INVENTION

The invention relates to a method for determining the interstitial oxygen concentration of a p-type doped semiconductor sample.

STATE OF THE ART

Silicon substrates intended for the microelectronics industry or for photovoltaic applications contain oxygen. When they are not in the form of precipitates, oxygen atoms generally occupy interstitial positions in the crystal lattice. In the case of single-crystal silicon, obtained by the Czochralski method, or in the case of solar-grade polysilicon, the interstitial oxygen concentration varies between $10^{17}$ and $2 \cdot 10^{18}$ atoms/cm$^3$.

The interstitial oxygen ($O_i$) has a significant impact on the mechanical and electric properties of silicon. In particular, at temperatures ranging between 200° C. and 500° C., the oxygen forms precipitates called Thermal Double Donors (TDD) which modify the electric properties of the material. At higher temperature, the oxygen forms other precipitates enabling to trap metal impurities present in the silicon. A getter effect can thus be obtained. Further, oxygen improves the mechanical properties of substrates by blocking the dislocations introduced by manufacturing processes.

For photovoltaic applications, a high oxygen concentration causes a performance decrease under illumination, especially a decrease in the conversion efficiency of photovoltaic cells containing boron-doped (B) silicon.

Knowing the interstitial oxygen concentration and distribution within the substrate thus appears to be important, to locally determine the influence of oxygen on the electric and mechanical properties of the silicon. Such information then enables to optimize crystallization or device manufacturing methods.

The oxygen concentration of a sample is conventionally determined by Fourier transform infrared (FTIR) spectroscopy. However, this technique is slow and lacks accuracy. It further requires a sample having a thickness of at least 200 μm and a preparation of the sample surface.

Article "Characterization of the oxygen distribution in Czochralski silicon using hydrogen-enhanced thermal donor formation" (A. G. Ulyashin et al., Materials Science and Engineering B73 124-129, 2000) describes another technique for determining the oxygen concentration.

This technique is based on the forming of thermal donors TDD. A hydrogen-plasma-enhanced heat treatment is applied to a P-type sample to form a PN junction. Then, the depth of the PN junction in the sample is determined by means of spreading resistance probe (SRP) measurements or capacitance-voltage (C-V) measurements. The thermal donor concentration is then calculated from the depth of the PN junction. A mathematical model enables to determine the oxygen concentration from the thermal donor concentration.

The used characterization methods require, just as the FTIR, a preparation of the sample. The SRP characterization requires tapering the sample to establish the resistance profile all along the sample depth. The C-V characterization uses metal contacts at the sample surface. Such contacts are difficult to remove without damaging or contaminating the sample material.

Due to the complexity of such characterization methods, the measurement technique of the above-mentioned article is slow and difficult to apply to substrates of microelectronics and photovoltaics.

Further, the substrate preparation and hydrogenation make this substrate impossible to use once the measurement has been performed.

SUMMARY OF THE INVENTION

A need therefore exists to provide a method which is fast and simple to implement, enabling to determine the interstitial oxygen concentration of a sample made from a group-IV p-type semiconductor material.

The sample comprising acceptor-type dopant impurities and having an initial charge carrier concentration and an initial resistivity, this need tends to be satisfied by the steps of:
  a) submitting the sample to a heat treatment to form thermal donors forming donor-type dopant impurities;
  b) determining the duration of the heat treatment required to obtain an impurity-compensated semiconductor material;
  c) determining the thermal donor concentration of the sample of compensated semiconductor material from the charge carrier concentration; and
  d) determining the interstitial oxygen concentration from the thermal donor concentration and the duration of the heat treatment.

After determining the interstitial oxygen concentration, a step of heat treatment at a temperature greater than or equal to 650° C. is further provided to restore the sample in its initial state.

BRIEF DESCRIPTION OF THE DRAWINGS

Other advantages and features will become more clearly apparent from the following description of particular embodiments given for non-restrictive example purposes only and illustrated by means of the appended drawings, in which.

DESCRIPTION OF A PREFERRED EMBODIMENT OF THE INVENTION

In a p-type doped silicon substrate, the free charge carriers are holes. Their number depends on concentration $N_A$ of dopant impurities implanted in the silicon, generally boron atoms (B). Such atoms are called electron acceptors.

When the substrate is essentially doped with boron, hole concentration $p_0$ is equal to the boron concentration: $p_0 = N_A = [B]$.

When the substrate further comprises electron donor atoms (for example, phosphorus), by a non-negligible concentration $N_D$, the initial concentration of free holes $p_0$ is equal to acceptor atom concentration $N_A$ minus donor atom concentration $N_D$: $p_0 = N_A - N_D$. This relation is valid if the acceptor and donor atoms are ionized only once. For donor and/or acceptor atoms ionized several times, degrees of ionization will be applied to concentrations $N_A$ and/or $N_D$ ($p_0=\alpha N_A-\beta N_D$).

Submitting the substrate to a temperature comprised between 200° C. and 500° C. will cause formation of thermal donors TDD in the substrate. Thermal donors generate electrons. They are thus considered as donor-type dopant impurities. Thermal donors are double donors since each TDD generates two free electrons.

When the concentration of acceptor-type dopant impurities is substantially equal to the sum of the concentrations in donor-type dopant impurities (phosphorus atoms and thermal donors), with concentrations eventually weighted by the degrees of ionization, the substrate is said to be impurity-compensated. This state of equilibrium actually corresponds to the transition between a p-type doped substrate (with a majority of holes) and an n-type doped substrate (with a majority of electrons).

It is here provided to detect this state of equilibrium during the anneal, to simply calculate thermal donor concentration $N_{TDD}$ and then deduce interstitial oxygen concentration $C_o$.

Figure 1:
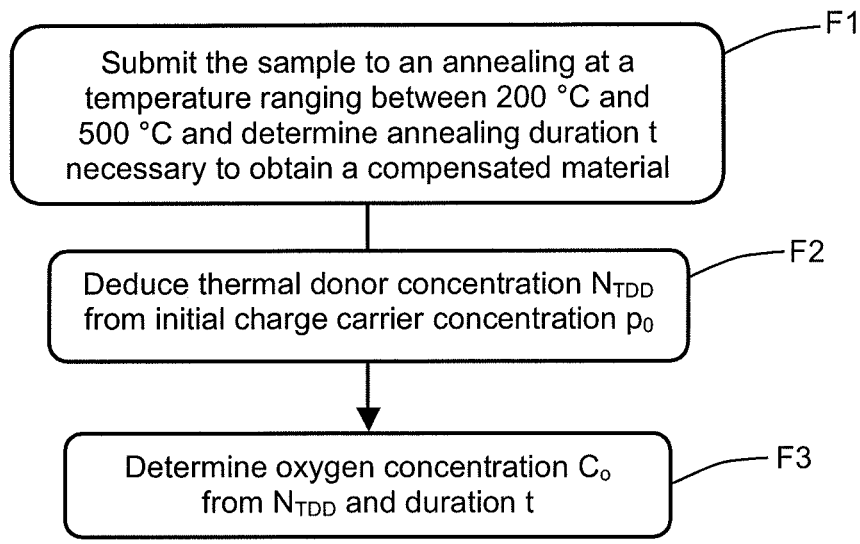
FIG. 1 shows steps of a method for determining interstitial oxygen concentration $C_o$ according to the invention.

FIG. 1 shows steps F1 to F3 of a method for determining interstitial oxygen concentration $C_o$ of a p-type semiconductor sample.

In a first step F1, a sample containing oxygen, for example, a silicon substrate, is submitted to a heat treatment, or annealing, to form thermal donors. The annealing temperature preferably ranges between 200° C. and 500° C., advantageously between 350° C. and 500° C. Indeed, as will be described hereafter, the kinetics of the formation of thermal donors is well known in this range of temperatures, especially at 450° C.

During annealing, the annealing duration t for which the silicon substrate is compensated is measured. Several techniques enabling to detect the compensated state of the silicon are detailed hereafter.

A first technique comprises measuring resistivity $\rho$ of the substrate during annealing.

It can be observed that the resistivity increases as thermal donors are being generated. This is due to the fact that the electrons originating from thermal donors compensate the substrate holes. Thus, the number of charge carriers tends towards zero. Once the compensation has been reached, the resistivity decreases since the number of charge carriers (electrons) increases.

Thus, the compensated state of silicon corresponds to a maximum resistivity. The silicon can then be considered as compensated when the resistivity exceeds a threshold value, preferably greater than 200 Ω·cm and greater than twice initial resistivity $\rho_o$ of the sample, that is, twice the resistivity before the thermal donor formation annealing.

The resistivity may be simply measured by the four-point probe method or by a contactless method, for example, by inductive coupling.

A second technique consists in detecting the change of the substrate conductivity type (from type p to type n) by measuring the conductivity type several times.

The determination of the conductivity type relies on the surface photo voltage (SPV) measurement method. Such a measurement is based on the following principle. A laser is periodically applied on the substrate surface, which will temporarily generate electron-hole pairs. The capacitive coupling between the surface and a probe enables to determine the surface voltage.

The difference between the surface voltage under illumination and the surface voltage in darkness, and more specifically the sign of this difference, enables to determine the conductivity type of the sample. The measurement of the conductivity type by the SPV method is, for example, performed by means of equipment PN-100 sold by the company SEMILAB.

Figure 2:
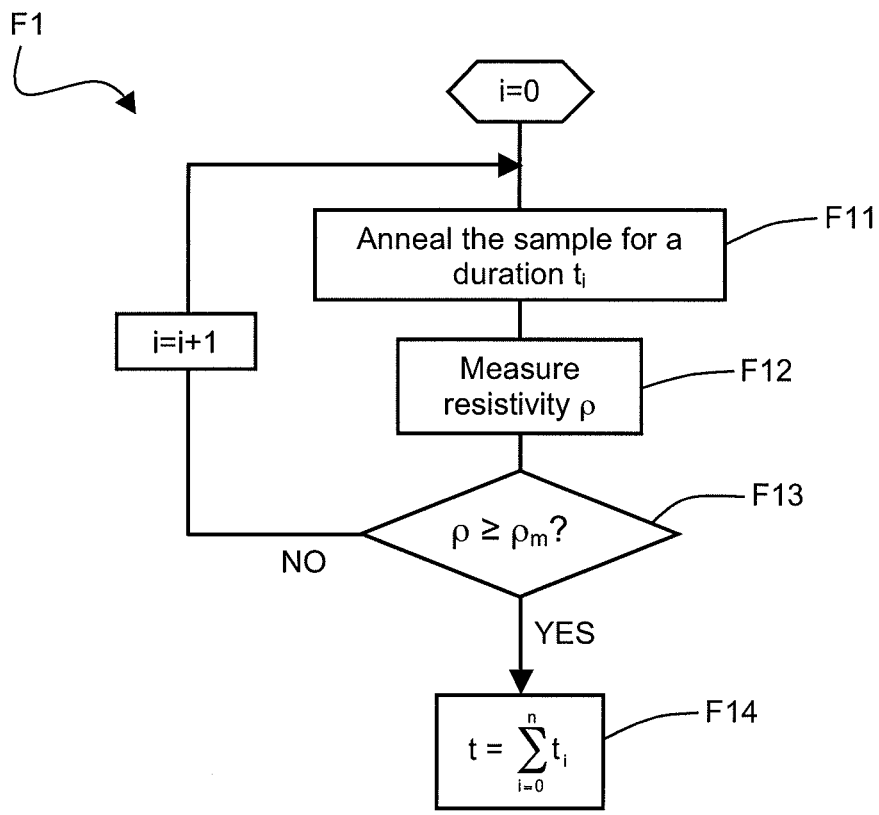
FIG. 2 shows an embodiment of annealing step F1 according to FIG. 1.

FIG. 2 shows an embodiment of annealing step F1 of FIG. 1. The annealing is carried out in several steps until the substrate resistivity reaches or exceeds a predetermined threshold. An index i, initially at zero, is used to count these steps.

At a step F11, the annealing is carried out for a time period $t_i$. Then, at a step F12, resistivity $\rho$ is measured. At F13, the measured value of the resistivity is compared with a threshold $\rho_m$ representative of the compensated state. If measured resistivity $\rho$ is lower than threshold $\rho_m$ (output NO of F13), it is looped back onto step F11 and index i is incremented. A new annealing step is then carried out for a time period $t_{i+1}$. Time period $t_{i+1}$ may be different from time period $t_i$. If measured resistivity $\rho$ is greater than threshold $\rho_m$ (output YES of F13), total annealing duration t applied to the substrate is calculated at F14, by adding time periods $t_i$ $$\left(t = \sum_{i=0}^{n} t_i\right).$$

Figure 3:
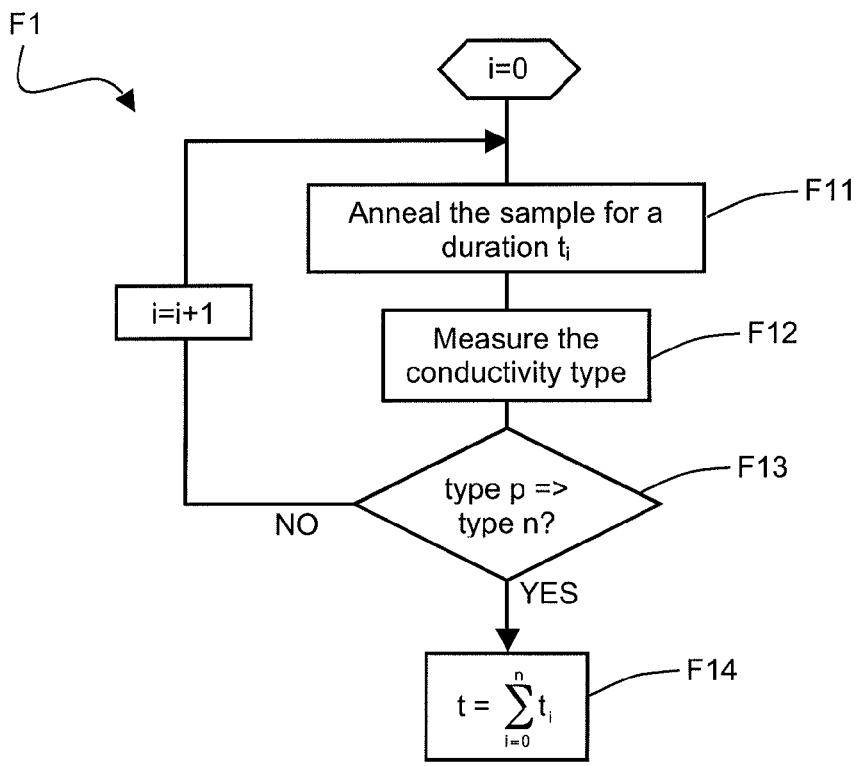
FIG. 3 shows an alternative embodiment of annealing step F1 according to FIG. 1.

FIG. 3 shows an alternative embodiment of steps of F12 and F13 of FIG. 2. Rather than the resistivity, the conductivity type is measured at F12, preferably by the SPV method. As long as the conductivity of the substrate is of type p (output NO of F13), steps F11 and F12 are repeated. However, as soon as the conductivity changes from type p to type n (output YES of F13), cumulated annealing duration t is calculated (F14).

Step F2 of the method of FIG. 1 comprises calculating thermal donor concentration $N_{TDD}$ of the compensated silicon, based on initial charge carrier concentration $p_0$. To achieve this, the fact that, in the compensated silicon, the concentration of acceptor-type impurities is equal to the sum of the concentrations of donor-type dopant impurities (weighted by their respective degrees of ionization) is used.

Donor-type impurities here correspond to thermal donors TDD and possibly to donor atoms $N_D$, for example, phosphorus, initially present in the substrate. Thus, in the most frequent case where the donor atoms ($N_D$) and the acceptor atoms ($N_A$) are ionized only once, the following is obtained:

$$2N_{TDD}+N_D=N_A \quad (1).$$

Thermal donors count double since they are doubly ionized.

Initial charge carrier concentration $p_0$ being, in this case, $N_A-N_D$, equation (1) becomes:

$$N_{TDD} = \frac{N_A - N_D}{2} = \frac{p_0}{2}. \quad (2)$$

Equation (2) thus enables to calculate thermal donor concentration $N_{TDD}$ obtained after an annealing of a duration t, knowing initial charge carrier concentration $p_0$ of the substrate.

Thus, for the calculation of thermal donor concentration $N_{TDD}$, relation (2), which reflects the optimum compensation will be used. In practice, this state of equilibrium is difficult to achieve during annealing. Thus, to determine annealing duration t, the silicon is considered to be compensated when the concentration of electrons generated by thermal donors ($2 \cdot N_{TDD}$) is equal to initial hole concentration $p_0$ ($p_0 = \alpha N_A - \beta N_D$), with an accuracy on the order of ±20%.

In other words, the compensated state is considered to have been reached when the following equation is satisfied:

$$0.8 \times p_0 \leq 2N_{TDD} \leq 1.20 \times p_0$$

With this approximation, the value of annealing duration t measured at step F1 is however close to that corresponding to the optimum compensation.

At step F3, interstitial oxygen concentration $C_o$ is determined from annealing duration t determined at step F1 and from thermal donor concentration $N_{TDD}$ calculated at step F2.

Interstitial oxygen concentration $C_o$ is preferably calculated by means of a relation provided in article "Formation kinetics of oxygen thermal donors in silicon" (Wijaranakula C. A. et al., Appl. Phys. Lett. 59 (13), pp. 1608, 1991). This article describes the kinetics of the formation of thermal donors in silicon by an annealing at 450° C.

This temperature further is a good compromise between the thermal donor formation speed and the maximum obtained concentration. A temperature higher than 450° C. favors the TDD formation speed to the detriment of the maximum concentration. A high temperature should thus be preferred when the oxygen concentration is assumed to be high, for example greater than $5 \cdot 10^{17}$ cm$^{-3}$. Conversely, a temperature lower than 450° C. will enable to increase the maximum TDD concentration and may be used for substrates having a low approximate oxygen concentration, for example, smaller than $5 \cdot 10^{17}$ cm$^{-3}$.

With no preliminary information relative to the oxygen concentration, an annealing temperature equal to 450° C. will preferably be chosen.

The relation expressing thermal donor concentration $N_{TDD}$ as a function of oxygen concentration $C_o$ and of anneal duration t is provided hereafter:

$$N_{TDD}(t, C_o) = 4.51 \cdot 10^{-52} \times \left( C_o \left[ 1 + \frac{2}{3} D_o \times t \times C_o^{2/3} \right]^{-3/2} \right)^{3.45} \times t^{1.02}, \quad (3)$$

$D_o$ being the interstitial oxygen diffusion coefficient $$\left( D_o = 0.13 \times e^{-\frac{2.53}{kT}} \right).$$

Knowing t and $N_{TDD}$ enables to calculate interstitial oxygen concentration $C_o$ of the substrate.

As a variant, interstitial oxygen concentration $C_o$ may be determined by means of charts of thermal donor concentration $N_{TDD}$ versus annealing duration t, for different values of oxygen concentration $C_o$.

Figure 4:
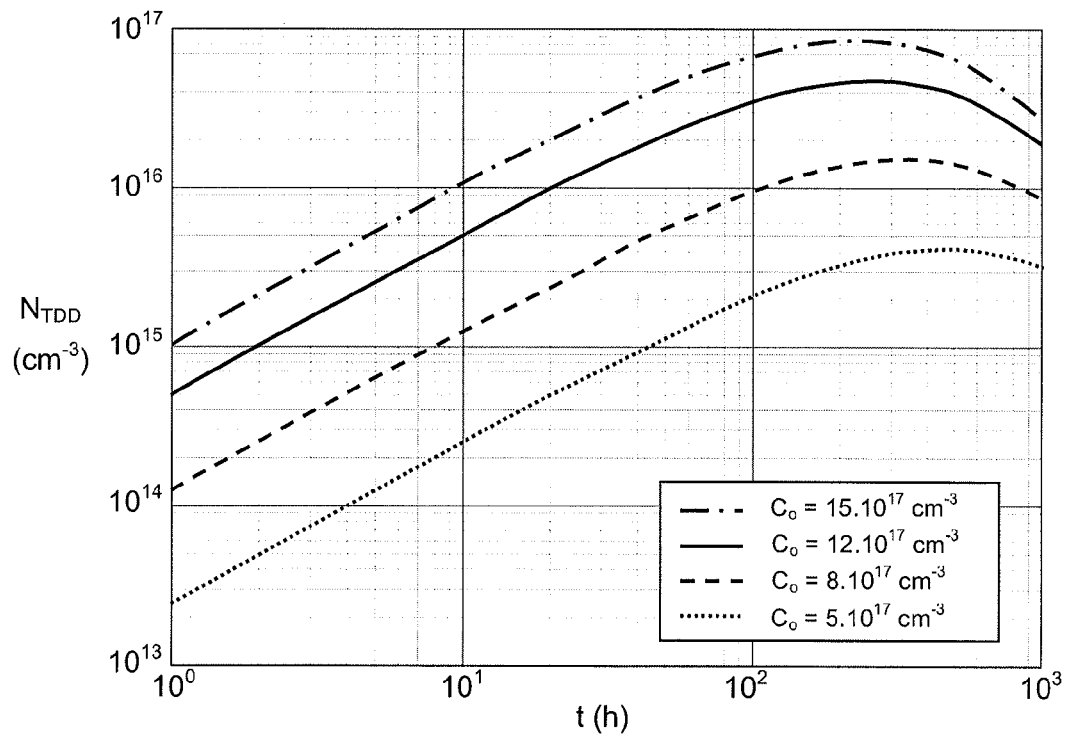
FIG. 4 shows charts of thermal donor concentration $N_{TDD}$ according to annealing duration t, for different values of interstitial oxygen concentration $C_o$.

FIG. 4 shows one of these charts, constructed based on relation (3) and for an annealing temperature of about 450° C.

It can be observed that a small variation of oxygen concentration $C_o$ causes a strong variation of thermal donor concentration $N_{TDD}$. For example purpose, after one hour of annealing, a substrate having an oxygen concentration equal to $5 \cdot 10^{17}$ cm$^{-3}$ forms $2.5 \cdot 10^{13}$ TDD per cm$^{-3}$, while a substrate with three times as large an oxygen concentration forms approximately 100 times more thermal donors.

The chart of FIG. 4 enables to determine the value of oxygen concentration $C_o$ in the measured substrate area, for a given concentration $N_{TDD}$ and a give anneal time t.

For an annealing temperature different from 450° C., relation (3) and the charts may be adapted, in particular thanks to the teachings of article "Effect of oxygen concentration on the kinetics of thermal donor formation in silicon at temperatures between 350 and 500° C." (Londos C. A. et al., Appl. Phys. Lett. 62 (13), pp. 1525, 1993). This article also described the kinetics of the forming of thermal donors in silicon, for annealing temperature ranging between 350° C. and 500° C.

The calculation of $N_{TDD}$ performed at step F2 requires knowing the value of charge carrier concentration $p_0$. This value is generally provided by the substrate supplier. If not, it may be determined in an additional step of the method of FIG. 1.

Figure 5:
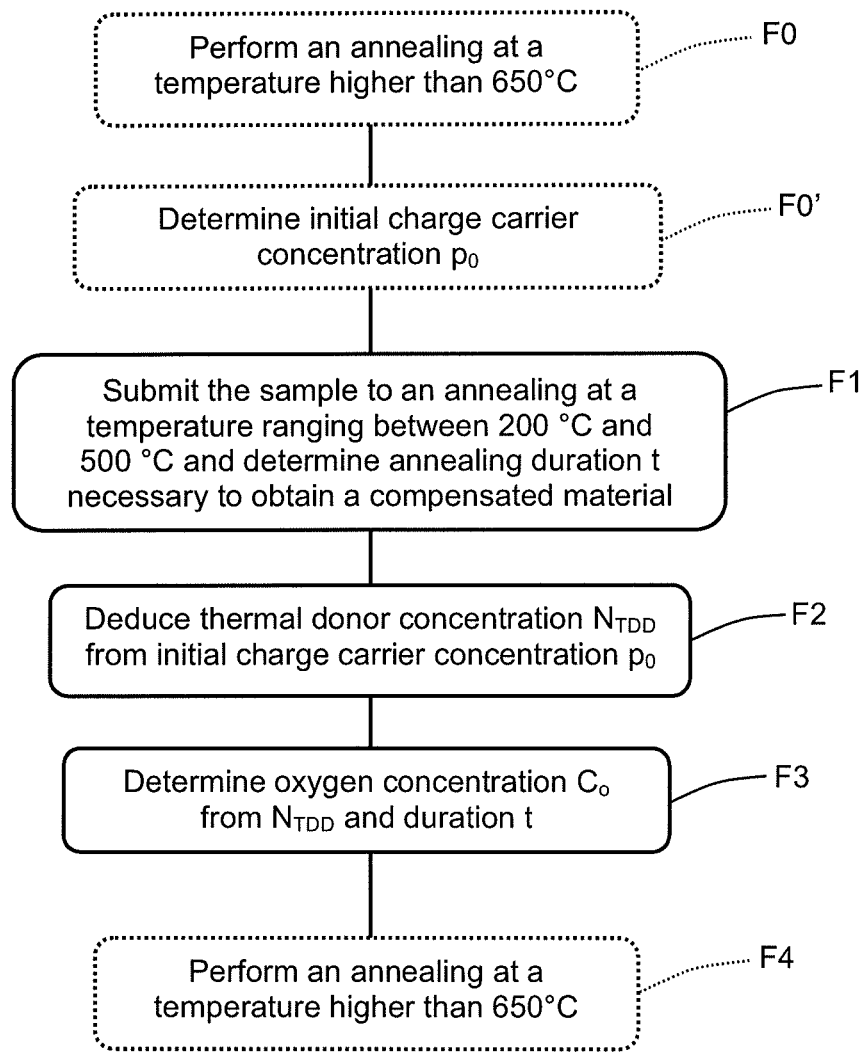
FIG. 5 shows additional steps of the method for determining interstitial oxygen concentration $C_o$ of FIG. 1.

FIG. 5 shows additional steps of the determination method, one of which enables to determine charge carrier concentration $p_0$.

When concentration $p_0$ is not known, the initial resistivity of the substrate may be measured before annealing at a step F0'. This measurement then enables to calculate the concentration of charge carriers (holes) $p_0$, by means of the following relation:

$$\rho_0 = \frac{1}{q \times p_o \times \mu_P}, \quad (4)$$

q being the elementary charge (q=$1.6 \cdot 10^{-19}$ C) and $\mu_p$ the mobility of holes in silicon.

Such a relation is only valid when the substrate essentially comprises acceptor atoms ($p_0 = N_A$), that is, when initial donor atom concentration $N_D$ is zero or neglected. It is considered that initial donor atom concentration $N_D$ is negligible when it is lower than one fifth of the concentration of acceptor-type dopant impurities $N_A$ ($N_D \leq \frac{1}{5} \cdot N_A$ or $5 \cdot N_D \leq N_A$).

If the substrate initially has both dopant types, donors and acceptors ($p_0 = N_A - N_D$), with a concentration $N_D$ greater than one fifth of concentration $N_A$ ($5 \cdot N_D \geq N_A$), then $p_0$ is determined with other methods such as Hall-effect measurements or absorption spectrometry.

To make sure that the substrate comprises no thermal donors in its initial state, which could distort the value of $p_0$, an annealing is preferably performed, at F0, at a temperature greater than or equal to 650° C. This makes precipitates of oxygen (or TDD thermal donors) unstable and eliminates them. Oxygen atoms then return to their interstitial positions. $p_o$ and $\rho_o$ are thus measured after such an annealing.

Annealing F0 may further be performed even though concentration $p_o$ is known, to make sure that thermal donor concentration $N_{TDD}$ is initially zero.

Such an annealing is preferably also used at the end of the process, at F4, after having determined the interstitial oxygen concentration in the desired area (F3). Due to annealing step F4, the substrate returns to its initial state and may be used again.

As an example, a thermal donor dissociation annealing (F0), at 650° C. for 30 min, is applied to a boron-doped silicon wafer. The wafer resistivity, measured by the four-point probe method (F0'), is approximately equal to 18.8 Ω·cm, which corresponds to an initial hole concentration $p_0$ (or a boron concentration $N_A$) on the order of $7.2 \cdot 10^{14}$ cm$^{-3}$ (equation (4): the material has a low donor atom concentration: $N_D < 10^{13}$ cm$^{-3}$).

The wafer is then submitted to several annealing steps (F11) at 450° C., of 15 minutes each, until the silicon is compensated. The conductivity type (FIG. 3; F12) is measured by the SPV method after each annealing step, by means of equipment PN-100 of SEMILAB.

The total annealing time to obtain the compensated silicon is 4.5 hours. Thus, after 4.5 hours of anneal, thermal donor concentration $N_{TDD}$ of the wafer is $3.6 \cdot 10^{14}$ cm$^{-3}$ ($p_0/2$). The interstitial oxygen concentration, calculated from relation (3), is equal to $7 \cdot 10^{17}$ cm$^{-3}$, in accordance with the value obtained by FTIR (between $6 \cdot 10^{17}$ cm$^{-3}$ and $9 \cdot 10^{17}$ cm$^{-3}$).

The determination method shown in FIG. 1 is fast and easy to implement since it implements simple characterization techniques. It further has a good accuracy, on the order of 5%, for the value of interstitial oxygen concentration $C_0$.

The method may advantageously be applied in several areas of the substrate, to totally map it. Each substrate area is then associated with the anneal duration t for which the area is compensated and the associated thermal donor concentration $N_{TDD}$ ($N_{TDD}=p_0/2$). Then, the interstitial oxygen concentration is calculated from the couple of values (t, $N_{TDD}$) for each substrate area. Such a mapping can then be used to optimize the device manufacturing.

Thermal donor concentration $N_{TDD}$ may be determined by a calculation step from initial charge carrier concentration $p_0$, as previously described. However, other techniques may be used, and especially a technique which determines concentration $N_{TDD}$ from the charge carrier concentration of the sample, measured after the anneal step (and no longer before). This technique is the following.

In an alternative embodiment of step F2, thermal donor concentration $N_{TDD}$ of the compensated silicon is determined from the charge carrier concentration measured immediately after the sample has changed conductivity type.

The charge carrier concentration after the passing from type p to type n is noted $n_o$ hereafter. It is measured for several temperatures T of the sample, for example, by Hall effect. An experimental curve $n_0(T)$ is then obtained from these temperature measurements.

The theoretical expressions of $n_0$ according to temperature are the following:

$$n_0(T) = \frac{N_D}{1 + 2\exp\left(\frac{E_F - E_D}{kT}\right)} + N_{TDD} \cdot \frac{\beta(T) \cdot (1 + 2 \cdot \alpha(T))}{1 + \beta(T) + 2 \cdot \alpha(T) \cdot \beta(T)} - N_A \quad (5)$$

$$n_0(T) = N_C(T) \cdot \exp\left(\frac{E_F - E_D}{kT}\right) \quad (6)$$

where $N_A$ and $N_D$ are the acceptor and donor dopant concentrations, $N_C$ is the state density in the conduction band, $E_F$ is the energy of the Fermi level, $E_D$ is the energy level of donor-type dopants, k is Boltzmann's constant, and T is the sample temperature.

$\alpha(T)$ and $\beta(T)$ are provided by the following expressions:

$$\alpha(T) = 0.5 \cdot \exp\left(\frac{E_2 - E_F(T)}{kT}\right),$$

and $$\beta(T) = 2 \cdot \exp\left(\frac{E_1 - E_F(T)}{kT}\right),$$

where $E_1 = E_C - 70$ meV and $E_2 = E_C - 150$ meV.

Thermal donor concentration $N_{TDD}$ is determined by having the theoretical curves provided by expressions (5) and (6) coincide with experimental curve $n_0(T)$ originating from the temperature measurements. In other words, the numerical values of $N_A$, $N_D$, and $N_{TDD}$ of equations (5) and (6) are varied until the theoretical curves superpose to measurement plot $n_0(T)$.

Many variants and modifications of the determination method described herein will occur to the man skilled in the art. The method has been described in relation with a silicon substrate. However, the method may also be applied to the other group-IV semiconductors, in particular germanium or silicon-germanium substrates. Indeed, germanium also is a semiconductor where thermal donors may be formed in the presence of oxygen.

We claim:

1. A method for determining an interstitial oxygen concentration of a sample made from a group-IV p-type semiconductor material, comprising acceptor-type dopant impurities and having an initial charge carrier concentration and an initial resistivity, comprising the step of:
   a) submitting the sample to a heat treatment to form thermal donors forming donor-type dopant impurities;
   b) determining a duration of the heat treatment required to obtain an impurity-compensated semiconductor material;
   c) determining a thermal donor concentration of the sample of compensated semiconductor material from the initial charge carrier concentration; and
   d) determining the interstitial oxygen concentration from the thermal donor concentration and the duration of the heat treatment.

2. The method according to claim 1, wherein the thermal donor concentration $N_{TDD}$ is determined from the initial charge carrier concentration $p_0$ by means of the following relation:

$$N_{TDD} = \frac{p_0}{2}.$$

3. The method according to claim 1, wherein step b) comprises the steps of:
   i) carrying out the heat treatment for a time period;
   ii) measuring a resistivity the sample, and
   iii) repeating steps i) and ii) until the resistivity of the sample exceeds a threshold value.

4. The method according to claim 3, wherein the threshold value is greater than 200 Ω·cm and greater than twice the initial resistivity of the sample.

5. The method according to claim 1, wherein step b) comprises the steps of:
   i) carrying out the heat treatment for a time period,
   ii) measuring a conductivity type of the sample, and
   iii) repeating steps i) and ii) as long as the sample has a p-type conductivity.

6. The method according to claim 5, wherein the measurement of the conductivity type is performed by a measurement of the surface photo voltage of the sample.

7. The method according to claim 1, initially comprising a heat treatment step at a temperature greater than or equal to 650° C. and a step of determining the initial charge carrier concentration.

8. The method according to claim 7, wherein the initial charge carrier concentration is determined by a resistivity measurement when the sample comprises donor-type dopant impurities by a concentration smaller than one fifth of the concentration of acceptor-type dopant impurities.

9. A method according to claim 7, wherein the initial charge carrier concentration is measured by Hall effect or by absorption spectrometry when the sample comprises donor-type dopant impurities by a concentration greater than one fifth of the concentration of acceptor-type dopant impurities.

10. The method according to claim 1, wherein the steps a) to d) are carried out in several areas of the sample to perform a mapping.

11. A method for determining an interstitial oxygen concentration of a sample made from a group-IV p-type semiconductor material, comprising acceptor-type dopant impurities and having an initial charge carrier concentration and an initial resistivity, comprising the step of:
   a) submitting the sample to a heat treatment to form thermal donors forming donor-type dopant impurities;
   b) determining a duration of the heat treatment required to obtain an impurity-compensated semiconductor material;
   c) determining a thermal donor concentration of the sample of compensated semiconductor material from the charge carrier concentration measured after the sample has passed from a p-type conductivity to an n-type conductivity; and
   d) determining the interstitial oxygen concentration from the thermal donor concentration and the duration of the heat treatment.

12. The method according to claim 11, wherein step b) comprises the steps of:
   i) carrying out the heat treatment for a time period;
   ii) measuring a resistivity of the sample,
   iii) repeating steps i) and ii) until the resistivity of the sample exceeds a threshold value.

13. The method according to claim 12, wherein the threshold value is greater than 200 Ω·cm and greater than twice the initial resistivity of the sample.

14. The method according to claim 11, wherein step b) comprises the steps of:
   i) carrying out the heat treatment for a time period,
   ii) measuring a conductivity type of the sample,
   iii) repeating steps i) and ii) as long as the sample has a p-type conductivity.

15. The method according to claim 14, wherein the measurement of the conductivity type is performed by a measurement of the surface photo voltage of the sample.

16. The method according to claim 11, initially comprising a heat treatment step at a temperature greater than or equal to 650° C. and a step of determining the initial charge carrier concentration.

17. The method according to claim 16, wherein the initial charge carrier concentration is determined by a resistivity measurement when the sample comprises donor-type dopant impurities by a concentration smaller than one fifth of the concentration of acceptor-type dopant impurities.

18. The method according to claim 16, wherein the initial charge carrier concentration is measured by Hall effect or by absorption spectrometry when the sample comprises donor-type dopant impurities by a concentration greater than one fifth of the concentration of acceptor-type dopant impurities.

19. The method according to claim 11, wherein the steps a) to d) are carried out in several areas of the sample to perform a mapping.

* * * * *